United States Patent
Brand et al.

(10) Patent No.: US 7,326,185 B2
(45) Date of Patent: Feb. 5, 2008

(54) VARIABLE-LENGTH NEEDLE COVERING DEVICE OF AN INJECTION DEVICE

(75) Inventors: Andreas Brand, Oberburg (CH); Remo Steiner, Muenchenbuchsee (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 10/233,281

(22) Filed: Aug. 30, 2002

(65) Prior Publication Data

US 2003/0050606 A1    Mar. 13, 2003

Related U.S. Application Data

(63) Continuation of application No. PCT/CH01/00112, filed on Feb. 22, 2001.

(30) Foreign Application Priority Data

Mar. 1, 2000    (DE)    ................ 100 09 815

(51) Int. Cl.
*A61M 5/00*    (2006.01)
(52) U.S. Cl. .................................... 604/110
(58) Field of Classification Search ............... 604/110, 604/192–199, 214–219, 187, 200, 264, 93.01, 604/164.01, 131, 118
See application file for complete search history.

(56) References Cited

U.S. PATENT DOCUMENTS

| | | | |
|---|---|---|---|
| 3,134,380 A | | 5/1964 | Armao |
| 3,601,509 A | * | 8/1971 | Kreitchman ................ 417/417 |
| 4,044,320 A | * | 8/1977 | Seinecke .................... 333/101 |
| 4,813,940 A | * | 3/1989 | Parry .......................... 604/198 |
| 4,892,521 A | * | 1/1990 | Laico et al. ................ 604/192 |
| 5,075,656 A | * | 12/1991 | Sun et al. ....................... 335/5 |
| 5,181,524 A | | 1/1993 | Wanderer et al. |
| 5,242,416 A | | 9/1993 | Hutson |
| 5,405,362 A | | 4/1995 | Kramer et al. |
| 5,688,241 A | | 11/1997 | Asbaghi |
| 6,019,622 A | * | 2/2000 | Takahashi et al. .......... 439/188 |
| 6,171,276 B1 | * | 1/2001 | Lippe et al. .................. 604/67 |
| 6,183,445 B1 | * | 2/2001 | Lund et al. ................. 604/198 |

* cited by examiner

Primary Examiner—Ann Y. Lam
(74) Attorney, Agent, or Firm—David E. Bruhn

(57) ABSTRACT

The invention relates to a needle covering device of an injection device, the injection device including a casing comprising a reservoir, in particular an ampoule, for a product fluid to be administered, and an injection needle for injecting the product fluid from the reservoir, wherein the device surrounds the injection needle in an extended position and exposes the injection needle in a retracted position. The device comprises a passage for the injection needle, a front section via which the device is placed on an injection point, and another section which is nearer to the casing than the front section is, at least in the extended position. The sections can be moved axially relative to the casing and relative to each other, such that the device is variable in its length, the front section being guided in a straight line on the casing.

10 Claims, 4 Drawing Sheets

VARIABLE-LENGTH NEEDLE COVERING DEVICE OF AN INJECTION DEVICE

CROSS-REFERENCE TO RELATED APPLICATION(S)

This application claims the benefit of PCT Application No. PCT/CHO1/00112, filed on Feb. 22, 2001, which claims priority to German Application No. DE 100 09 815.0, filed on Mar. 1, 2000, both of which are herein incorporated by reference in their entirety.

BACKGROUND OF THE INVENTION

1. Field of the Invention

The invention relates to a variable-length needle cover for an injection device.

2. Description of the Related Art

Many users of injection devices have a psychological aversion (so-called "needle phobia") to injection needles such as those used for injecting a fluid product. Patients who actually inject the fluid product themselves often have an inhibition threshold that has to be overcome when injecting the needle. In order to reduce this inhibition threshold, needle covers have been provided for injection devices.

A variable-length needle covering device for a syringe is disclosed in WO 96/11026. The needle covering device has a porous foam material or a flexible polyethylene film. When the needle covering device is retracted, the cover is either unguided in movement or only guided by the injection needle itself. If the syringe is placed on the skin at any non-perpendicular angle to the surface of the skin, the injection needle may pierce the needle covering device.

SUMMARY OF THE INVENTION

The present invention provides a needle covering device for an injection device that only requires a relatively small amount of space and may be securely operated. Operation of the needle covering device is relatively simple.

In one embodiment, the injection device includes a casing having a reservoir or storage container, such as an ampoule, containing the fluid product. The injection device also includes a needle for injecting the fluid product from the reservoir. A needle cover surrounds the needle when the needle is in an extended position so that the needle is generally visually obscured. The needle covering device may protrude beyond the needle. When in a retracted position, the covering device exposes the needle.

In addition, the injection device may include a passage for the injection needle and a protective cap (if so provided in one embodiment). A front section may be provided that serves as an injection point. A second section may be provided that, when in the extended position, is nearer the casing than the front section is. The sections can be moved axially relative to the casing and each other, such that the device is variable in length. A distance between a front and a rear end of the device is variable. The front section of the device is guided in a straight line on the casing. In this way, the sections are guided in a straight line in the direction of the longitudinal axis of the injection needle. The sections are thus securely guided in a straight line, without the injection needle being deflected or strained. The needle covering device can be guided in a straight line within itself or directly on the casing. In each case, it is guided in a straight line with respect to the casing, i.e., relative to the casing.

In one embodiment, the second section has no contact with the injection point when in the extended position, but in the retracted position the second section can be placed on the injection point just like the front section. Both sections can be guided directly on the casing. In one embodiment, the front and second sections are guided on the casing. In another embodiment, the second section is guided on the casing, and the front section is guided on the second section. The front section is therefore indirectly linearly guided on the casing, via the second section. In either case, the sections can be guided by a rear section or adapter section which is fixedly connected to the casing and is axially rigid (that is, fixed or rigid along an axial direction that is defined by the needle) within itself.

In one embodiment, the front section of the needle covering device may be axially rigid. The front section is therefore not generally variable in its axial length. This allows the front section to be guided securely on the casing. A front section that is axially rigid also allows the device to be precisely placed on the injection point. The front section may have a flat front area through which the front section is placed on the injection point.

In one embodiment, the sections of the device may be telescopic. All of the sections may then be axially rigid. The individual sections of the needle covering device can be slid within each other in such a way that the needle covering device is variable in its length. In the retracted position, the individual telescopic sections can be arranged within each other (and not axially offset), thus achieving a smaller axial length of the needle covering device. Thus, a relatively small, efficient, non-buckling needle covering device is provided. The telescopic sections may be formed by sleeves that can be slid from a position in which the sleeves have a minimum axial overlap to a position in which they have a maximum, possibly complete, axial overlap. In the position of maximum overlap, the needle covering device is in the retracted position. The individual telescopic sections or sleeves may be of equal length and come to rest directly side by side in the retracted position. A telescopic needle covering device according to this embodiment includes at least two telescopic sections.

In one embodiment, when the cover is in the extended position, the other telescopic section protrudes out of the casing or adapter section and the front telescopic section protrudes out of the second telescopic section. In the retracted position, both telescopic sections are slid back into the casing or adapter section. The adapter section is fixedly connected to the casing so as to form a guide for a telescopic section adjacent to and movable with respect to the adapter section. The adapter section can be formed by a telescopic receptacle. The telescopic sections can be slid into the adapter section to move to the retracted position. Such a needle covering device may be connected to a conventional injection device lacking a needle covering device, without significant changes having to be made to said injection device. Thus, when the covering device is not slid into the casing of the injection device it may still secure guidance of the needle covering device.

In one embodiment, the telescopic sections may be axially guided in a straight line. The telescopic sections may be sleeve-shaped. The outer and/or inner surface areas of the telescopic sections can form the guiding areas. The telescopic sections may also be non-rotationally axially guided. Adjacent telescopic sections may include grooves and protrusions respectively, that interconnect with each other to prevent the telescopic sections from rotating. Instead of circular sleeves, the telescopic sections can instead be formed by oval or cornered sleeves that also prevent rotation.

In one embodiment, the needle covering device may include a concertina wall or be formed by a concertina wall. The front section of the concertina wall is preferably rigid. The section of the concertina wall that effects the variable length is arranged between the casing and the front section of the concertina wall. Through a front restraint on the front section and a rear restraint on the casing or an adapter section fixedly connected to the casing, the concertina wall is also axially guided in a straight line when the length is varied.

In one embodiment, the front section of a needle covering device is slide guided in a straight line by a guiding body. The guiding body is fixedly connected to the front section and projects from the front section into the casing of the injection device or into a rear section of the needle covering device. The guiding body is slide-mounted in the casing and/or in the rear section. The guiding body may be a rod or an elongated lamina. A number of guiding bodies may also be provided. Such a guiding body is connected to the front section of the telescopic needle covering device or of the concertina wall. In a telescopic needle covering device, the guiding body is formed directly by the telescopic sections. The guiding body of the front telescopic section is then the other telescopic section adjacent to said section.

In one embodiment, an adapter element may be provided for attaching the needle covering device. The adapter element can be directly attached to the ampoule or a guiding tube for the ampoule, or is fixedly connected to the casing. The needle covering device is, for example, connected to the adapter element via a bayonet lock. It can, however, also be screwed on or plugged on. In the case of a latch connection, an elastic clip of the needle covering device is pushed over a bulged ring or other protrusion of the adapter element, thus generating a connection.

In one embodiment, the needle covering device may be held by an elasticity force in its extended position. A pressure spring is provided between the casing or the adapter section and the front section. From the retracted position the spring automatically presses the front section into the extended position, at least partially slaving the other section.

The fluid product may be automatically injected when the injection needle is correctly positioned. This depends on the correct penetration depth of the injection needle into the tissue. When using the needle covering device there is a relationship between the variation in the length of the needle covering device and the penetration depth of the injection needle. The needle covering device may be formed so that the desired penetration depth of the needle is achieved in the retracted position of the needle covering device. The retracted position of the needle covering device can be adjusted as desires.

In one embodiment, a contact is provided that causes automatic delivery of the fluid product. The contact is activated in the retracted position. In the retracted position, the front section preferably presses against a switch that lies opposite the placing area on the injection needle. A contact body may be used that is connected to the front section and protrudes into the casing, at least in the retracted position. In this position, the front section provides that the fluid product is automatically delivered. A mechanical, electrical or magnetic contact (e.g., a Reed contact or an iron-plastic Reed contact), may be used. The contact body may be an axially extending rod.

DETAILED DESCRIPTION

Figure 1:
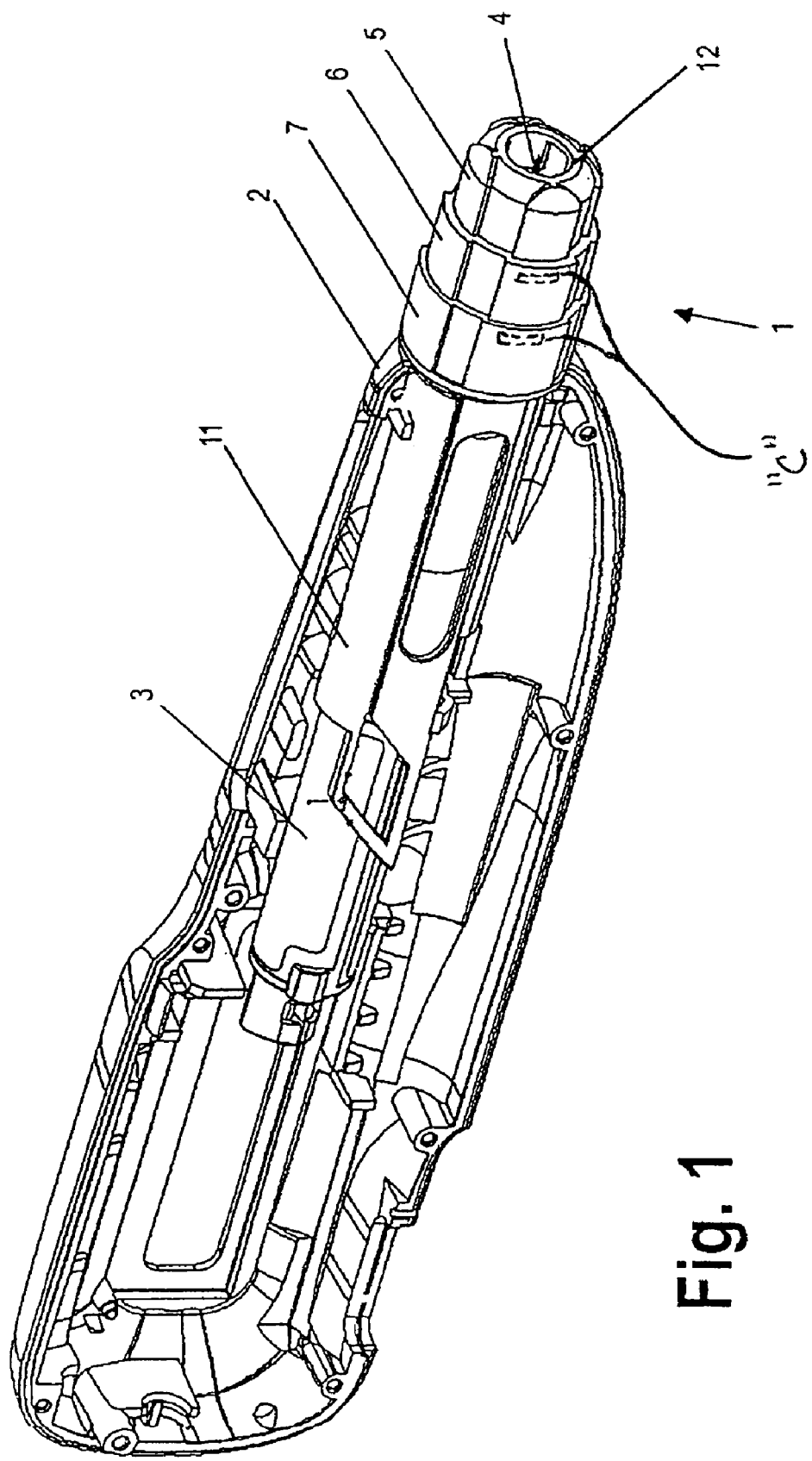
FIG. 1 is a partially sectioned view of an injection device having a telescopic needle covering device.

Referring to FIG. 1, a casing 2 is illustrated. The casing 2 has two casing halves (only one such half being shown). An ampoule 3 is accommodated in the casing 2 as a reservoir for a product fluid to be administered. The ampoule 3 is held in the casing 2 by a guiding tube 11 which is fixedly connected to the casing 2. The ampoule 3 comprises an outlet end and a piston, wherein the piston is pressed towards the outlet end in order to deliver the fluid product. An injection needle 4 has a fluid connection to the outlet end of the ampoule 3. The fluid product is injected via the injection needle 4.

The injection needle 4 is at least partially surrounded by a needle covering device 1, such that the injection needle 4 is substantially obscured from view.

In the embodiment illustrated in FIG. 1, the needle covering device 1 is telescopic. The needle covering device 1 is fixedly connected to the casing 2 via a rear section 7, referred to as an adapter section 7. An intermediate section 6 and a front section 5 form two telescopic sections of the needle covering device. In FIG. 1, the needle covering device 1 is shown in its extended position. In this position, the needle covering device is biased by an interior spring (see, for example FIG. 4, wherein spring "S" is shown) which presses the front section 5 away from the casing 2.

A contact C may be provided to cause automatic delivery of the fluid product. The contact C is activated in the retracted position. In the retracted position, the front section 5 preferably presses against a switch that lies opposite the placing area on the injection needle. A contact body may be used that is connected to the front section 5 and protrudes into the casing 2, at least in the retracted position. In this position, the front section 5 provides that the fluid product is automatically delivered. The contact C may be, for example, a mechanical, electrical or magnetic contact (e.g., a Reed contact or an iron-plastic Reed contact). The contact body may be an axially extending rod (for example, contact body 9 of FIG. 2c).

Figure 2A:
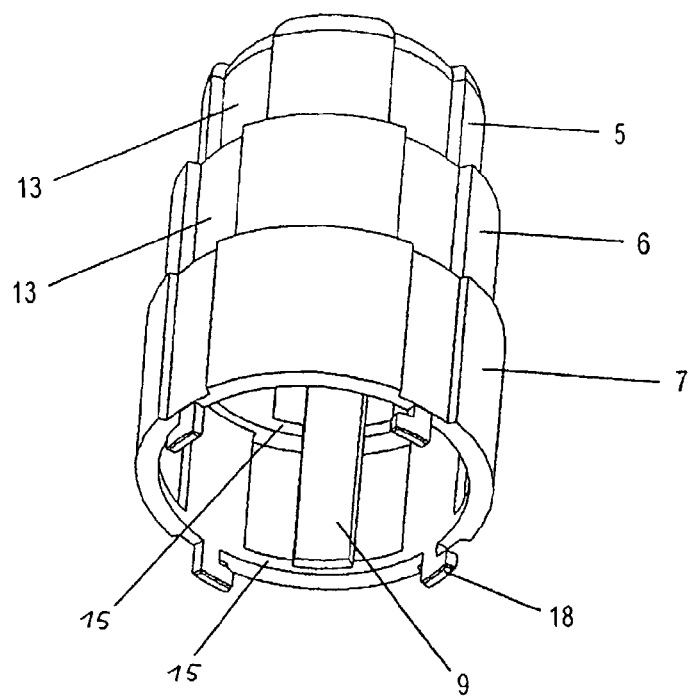
FIG. 2a illustrates a perspective view of a telescopic needle covering device in an extended position in accordance with one embodiment of the present invention.
Figure 2B:
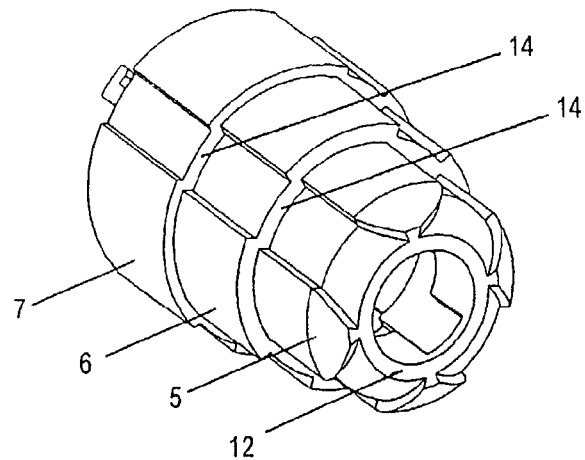
FIG. 2b illustrates another perspective view of a telescopic needle covering device in an extended position in accordance with one embodiment of the present invention.
Figure 2C:
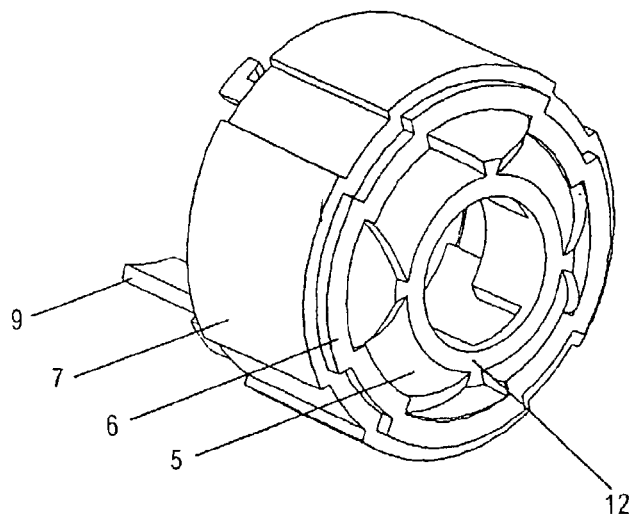
FIG. 2c illustrates yet a view of a telescopic needle covering device in a retracted position in accordance with one embodiment of the present invention.

FIGS. 2a-2c illustrate the telescopic needle covering device 1. The sections 5, 6 and 7 are sleeve-shaped or hollow cylinders. Four longitudinal grooves 13 are uniformly spaced on the outer surface area of each of the sections 5 and 6. Protrusions 14 are provided that interconnect with one of the grooves 13. The protrusions 14 are formed on the inner surface areas of each of the sections 6 and 7. The sections 5 and 6 can be linearly slid along the grooves 13. In this way, the sections 5 and 6 are also prevented from rotating. The maximum retracted position of the needle covering device 1 is defined by stoppers 15. There are also stoppers that define the maximum extended length, which are not shown. In their retracted position, the sections 5, 6 and 7 sit concentrically inside each other. The sections 5, 6 and 7 may be made of plastic.

A guiding body 9, or contact body, includes a flat, elongated member. The guiding body 9 is fixedly connected to the front section 5. When the front section 5 is retracted, the guiding body 9 is guided in a corresponding receptacle into the casing 2.

The needle covering device 1 is shown in a retracted position in FIG. 2c. The guiding body 9 projects backwards from the rear end of the needle covering device 1 into the casing 2. In this position, the guiding body 9 preferably closes a contact for automatically delivering the fluid product. In this way, it also forms a contact body 9. The body 9 can also be embodied as a contact body 9 only, without a guiding function.

The needle covering device 1 can be fixedly connected to the casing 2, the ampoule 3 or the guiding tube 11. An adapter element 10 may be provided for connecting the needle covering device 1. Various adapter elements 10 are illustrated in FIGS. 3a and 3b.

Figure 3A:
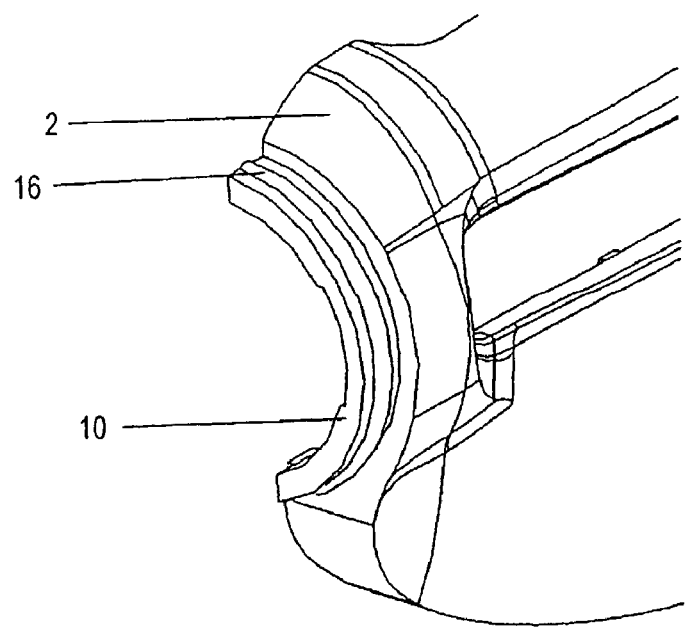
FIG. 3a illustrates one manner of attaching a needle covering device to an injection device in accordance with one embodiment of the present invention.

FIG. 3a shows an adapter element 10 having a bulged ring 16 on an outer surface area. The adapter element 10 is fixedly connected to the casing or formed on the casing as one piece. As an adapter counter element, the needle covering device 1 would have one or more elastic clips at its rear end. The clips are pushed over the bulged ring 16 to connect to the casing to establish an annular latching connection. Such an adapter element 10 for such an annular latching connection can also be formed on the ampoule 3 or the guiding tube 11.

Figure 3B:
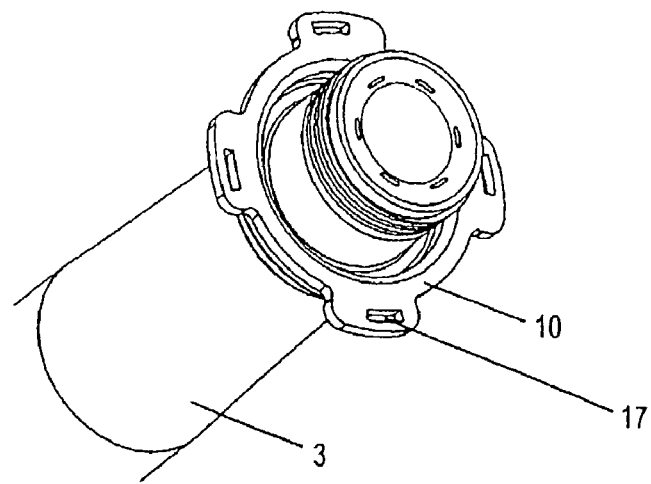
FIG. 3b illustrates another manner of attaching a needle covering device to an injection device in accordance with one embodiment of the present invention.
Figure 3C:
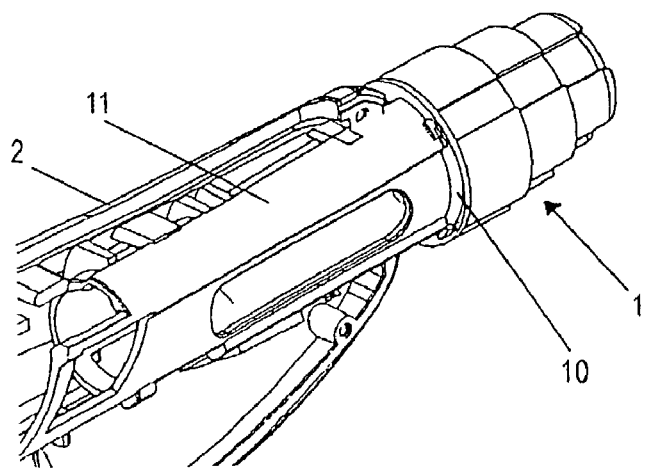
FIG. 3c illustrates yet another manner of attaching a needle covering device to an injection device in accordance with one embodiment of the present invention.

FIG. 3b shows an adapter element 10 for a bayonet connection, such as that used in FIGS. 1, 2a, 2b and 2c. Here, the adapter element 10 may be connected directly to the ampoule 3. FIG. 3c shows a needle covering device 1 attached to the guiding tube 11 by means of a bayonet connection.

In a flange-like widening of the bayonet type adapter elements 10, four recesses or openings 17 are uniformly distributed over the circumference. An adapter counter element in the form of connecting hooks 18 (FIG. 2a) of the needle covering device 1 is inserted into the recesses or openings 17. The whole needle covering device 1 is then turned in such a way that the connecting hooks 18 in the recesses 17 ensure a positive or frictional connection between the needle covering device 1 and the adapter element 10. Such an adapter element 10 for the bayonet connection can be formed on the casing 2, the ampoule 3 or the guiding tube 11. Conversely, the adapter element and adapter counter element could be switched relative to the casing, the ampoule or the guiding tube and the needle covering device 1.

Figure 4:
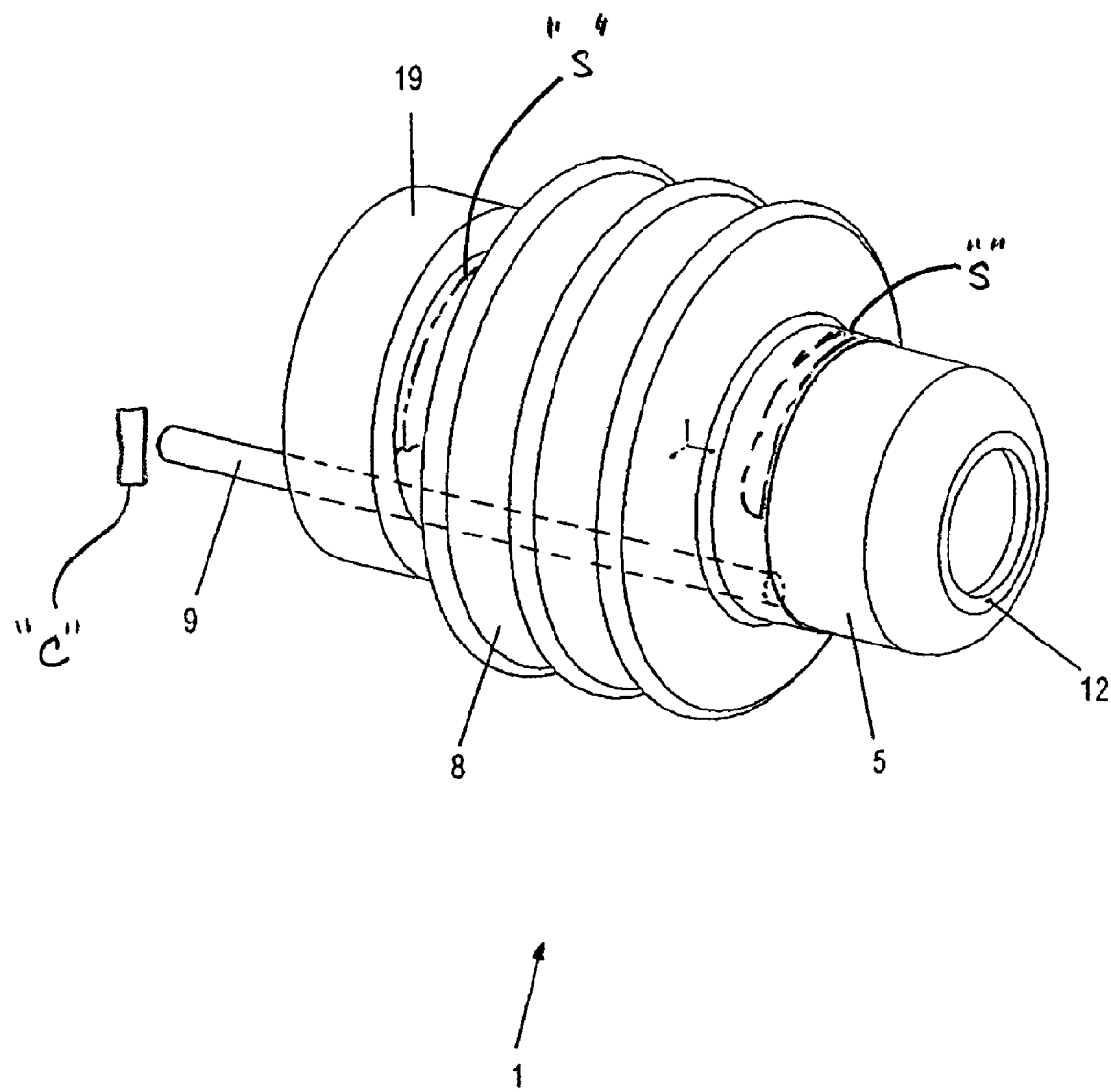
FIG. 4 illustrates a needle covering device having a concertina wall.

FIG. 4 shows a needle covering device 1 comprising a concertina wall 8 or similar bellows type structure. The concertina wall 8 is formed between the front section 5, which is rigid and a connecting section 19. The connecting section 19 can be connected to the injection device in the manner described above, wherein an adapter counter element is not shown. The guiding body 9 may be extended into the casing 2 (not shown), through the concertina wall 8 to guide the front section 5. Alternatively, the guiding body 9 may simply extend from the front section 5, through the concertina wall 8, and to the connecting section 19, so long as the needle covering device 1 is smoothly guided in a straight line relative to the casing.

Since the guiding body 9 may be linearly slide-guided in the casing 2, the concertina wall 8 is prevented from jamming when the needle covering device 1 is placed on the tissue at an angle, i.e., when lateral forces are present. The guiding body 9 can also activate a contact for automatically delivering the fluid product, in addition to or instead of serving as a guide. The front section 5 is held in its extended position by a restoring element, preferably a spiral spring "S". The concertina wall 8 may be made of a flexible plastic while the front section 5 and the connecting section 19 are made of a rigid plastic.

In the foregoing description various embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

We claim:

1. An injection device comprising:
   a casing having a reservoir for a fluid product and an injection needle; and
   a needle covering device, wherein the needle covering device comprises:
   a rear section for attaching the needle covering device to the injection device;
   a retractable front section nondetachably coupled to the rear section and linearly and axially moveable through a range of motion relative to the rear section so as to define an extended position that substantially surrounds the injection needle and a retracted position that exposes the injection needle, wherein a portion of the front section may be abutted against a surface to be injected and the front section is moveable through said range of motion generally freely; and
   a magnetic contact for activating the automatic delivery of said fluid product, the magnetic contact coupled to the retractable front section, wherein the magnetic contact extends through the rear section into the casing when the retractable front section is in the retracted position to activate the injection device.

2. The injection device of claim 1, wherein the retractable front section is axially rigid.

3. The injection device of claim 1, wherein said front section and said rear section are telescopic with respect to one another.

4. The injection device of claim 3, further comprising a guide bar coupled to the needle covering device and a receptacle connected to the casing, wherein the receptacle forms a guide for the guide bar.

5. The injection device of claim 3, wherein said front section and said rear section are prevented from rotating with respect to one another.

6. The injection device of claim 1, further comprising a guiding body wherein said front section is slide-guided in a straight line on said casing by the guiding body.

7. The injection device of claim 1, wherein the retractable front section includes a spring, and the retractable front section is urged to the extended position by force of the spring.

8. An injection device comprising:
- a casing for enclosing a reservoir for a fluid product and an injection needle; and
- a needle covering device, wherein the needle covering device comprises:
  - a rear section for attaching the needle covering device to the injection device;
  - a retractable front section nondetachably coupled to the rear section and linearly and axially moveable through a range of motion relative to the rear section so as to define an extended position that substantially surrounds the injection needle and a retracted position that exposes the injection needle, wherein a portion of the front section may be abutted against a surface to be injected and the front section is moveable through said range of motion generally freely; and
- a Reed contact for activating the automatic delivery of said fluid product, the Reed contact coupled to the retractable front section, wherein the Reed contact extends through the rear section into the casing when the retractable front section is in the retracted position to activate the injection device.

9. The injection device of claim 8, wherein the Reed contact is an iron-plastic Reed contact.

10. An injection device comprising:
- a casing for enclosing a reservoir for a fluid product, an injection needle; and
- a needle covering device, wherein the needle covering device comprises:
  - (a) a rear section for attaching the needle covering device to the injection device;
  - (b) a retractable front section nondetachably coupled to the rear section and linearly and axially moveable through a range of motion relative to the rear section so as to define an extended position that substantially surrounds the injection needle;
  - (c) a retracted position that exposes the injection needle, wherein a portion of the front section may be abutted against a surface to be injected and the front section is moveable through said range of motion generally freely, and wherein the front section in the retracted position presses against a switch that lies opposite a placing area on the injection needle; and
  - (d) a magnetic contact for activating the automatic delivery of the fluid product, the magnetic contact connected to the retractable front section, wherein the magnetic contact extends through the rear section into the casing when the retractable front section is in the retracted position to activate the injection device.

* * * * *